United States Patent [19]

Kasai et al.

[11] Patent Number: 5,274,086

[45] Date of Patent: Dec. 28, 1993

[54] N-ACETYL-β-D-GLUCOSAMINE DERIVATIVES AND REAGENTS FOR DETERMINING N-ACETYL-β-D-GLUCOSAMINIDASE ACTIVITY CONTAINING THE SAME AS EFFECTIVE INGREDIENTS

[75] Inventors: Kouichi Kasai; Kiyoshi Okada; Nobuyuki Yamaji, all of Noda, Japan

[73] Assignee: Kikkoman Corporation, Noda, Japan

[21] Appl. No.: 806,374

[22] Filed: Dec. 13, 1991

[30] Foreign Application Priority Data

Dec. 20, 1990 [JP] Japan .................. 2-411776

[51] Int. Cl.$^5$ .................. C07H 15/24; C07H 17/00
[52] U.S. Cl. .................. 536/17.2; 536/17.6; 536/18.1; 536/53; 536/122; 435/18; 435/4
[58] Field of Search .................. 536/18.1, 55.2, 17.2, 536/17.9, 18.6, 4.1, 55.3, 120, 115, 117, 119, 53

[56] References Cited

U.S. PATENT DOCUMENTS 3,524,844 8/1970 Keller-Juslen .................. 538/18.1
5,030,721 7/1991 Kasai et al. .................. 536/4.1

FOREIGN PATENT DOCUMENTS 63-309199 12/1988 Japan .

OTHER PUBLICATIONS

"Methods in Enzymology", vol. 28, pp. 702–713 (1972).
Dance, N., et al., "Clinica Chimica Acta", vol. 24, pp. 189–197 (1969).
Noto, A., et al., "Clin. Chem.", vol. 29, No. 10, pp. 1713–1716 (1983).
Makise, J., et al., "Clin. Chem.", vol. 34, No. 10, pp. 2140–2143 (1988).

*Primary Examiner*—Johnnie R. Brown
*Assistant Examiner*—Everett White
*Attorney, Agent, or Firm*—Banner, Birch, McKie & Beckett

[57] ABSTRACT

N-Acetyl-β-D-glucosamine derivatives represented by the formula

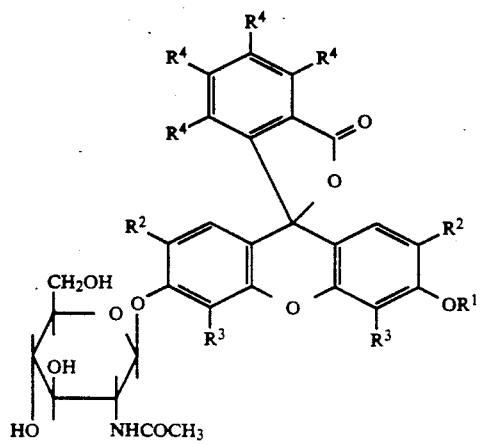

wherein $R^1$ denotes a substituted alkyl group of 1 to 4 carbon atoms having a hydroxyl group, carboxyl group, sulfonic acid group or phosphoric acid group, or an alkali metal salt thereof, or a substituted phenyl group having a hydroxyl group, carboxyl group, sulfonic acid group, phosphoric acid group or said substituted alkyl group, or an alkali metal salt thereof, and $R^2$, $R^3$ and $R^4$ each independently denote a hydrogen atom, halogen atom or nitro group, a process for producing the same, reagents for determining N-acetyl-β-D-glucosaminidase activity containing said derivatives as effective ingredients, and a method for determining N-acetyl-β-D-glucosaminidase activity using said derivatives.

6 Claims, 1 Drawing Sheet

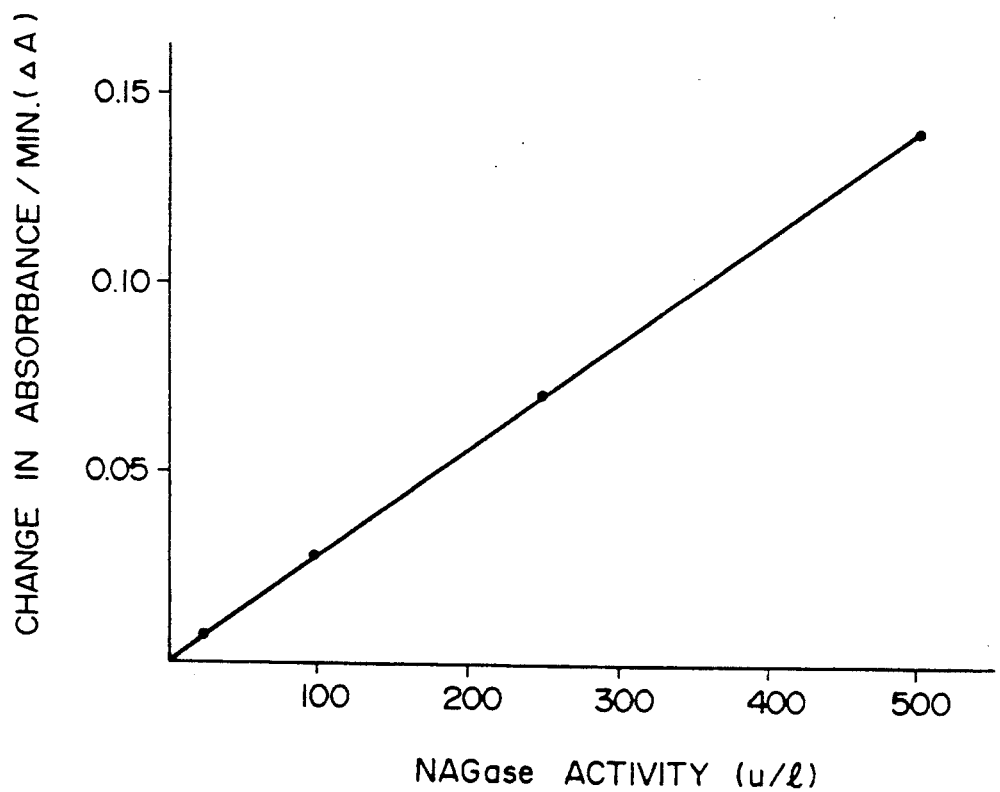
F I G. 1

N-ACETYL-β-D-GLUCOSAMINE DERIVATIVES AND REAGENTS FOR DETERMINING N-ACETYL-β-D-GLUCOSAMINIDASE ACTIVITY CONTAINING THE SAME AS EFFECTIVE INGREDIENTS

BACKGROUND OF THE INVENTION

1. Field of the Invention

The present invention relates to novel N-acetyl-β-D-glucosamine derivatives, a process for producing the same, reagents for determining N-acetyl-β-D-glucosaminidase activity containing the derivatives as effective ingredients, and a method for determining N-acetyl-β-D-glucosaminidase activity efficiently and accurately by using the derivatives.

2. Description of the Prior Art

N-Acetyl-β-D-glucosamidase (hereinafter simply referred to as NAGase) is one of the enzymes in lysosomes distributed in the kidney tubular epithelium in large quantities, and participates in decomposition of glucoproteins and mucopolysaccharides. It is recognized that the amount of urinary NAGase increases in various renal diseases such as acute renal deficiency, glomerulonephritis, etc. or in post-operative kidney. It is also recognized that in the case of diabetes the amount of NAGase increases not only in urine but also in serum. As an aid for diagnosis and course observation of various such renal diseases and also as an index in studies on renal toxicity of drugs, the determination of NAGase activity has attracted much attention both in clinical fields and in animal experiments.

Substrates for use in determining NAGase activity hitherto known include, for example, p-nitrophenyl-N-acetyl-β-D-glucosaminide [Methods Enzymol., 28, 702 (1972)], 4-methylumbelliferyl-N-acetyl-β-D-glucosaminide [Clinica. Chimica. Acta., 24, 189 (1969)]and m-cresolsulfonephthaleinyl-N-acetyl-β-D-glucosaminide [Clin. Chem., 29, 1713 (1983)].

However, the use of these compounds as the substrate for determining NAGase activity has a drawback in that aglycone formed by the action of enzyme must be determined in such a highly alkaline pH region of the reaction solution as about 10 to 11, so that the determination of enzyme activity can be made only by means of so-called end-point assay, in which the enzyme reaction is once discontinued to perform the determination of the enzyme activity, while the rate-assay method, which is the most suitable as the method for determining enzyme activity in most cases, cannot be used.

Recently, as substrates which can be used in said rate-assay method, in which enzyme activity is determined by directly measuring changes in absorbance while the enzyme reaction is in progress, there have been proposed 2-chloro-4-nitrophenyl-N-acetyl-β-D-glucosaminide [Clin. Chem., 34, 2140 (1988)]and sodio-3,3'-dichlorophenolsulfonephthaleinyl-N-acetyl-β-D-glucosaminide [Japanese Patent Application Kokai (Laid-open) No. 63-309199].

However, these compounds have drawbacks in that neither of them can exhibit sufficient sensitivity at pH of 4.5–5.0, which is the optimum pH for NAGase, and further 2-chloro-4-nitrophenyl-N-acetyl-β-D-glucosaminide cannot be dissolved in amounts necessary and sufficient for the determination of NAGase activity.

In this connection, some of the present inventors have lately proposed resorufinyl-N-acetyl-β-D-glucosaminide or resazurinyl-N-acetyl-β-D-glucosaminide as a substrate which can be effectively used in the rate-assay method (U.S. Pat. No. 5,030,721). However these substrates were not necessarily satisfactory in solubility in water.

The object of the present invention is to provide, overcoming the problems mentioned above involved in previous reagents for determining NAGase activity and in methods of determination using the reagents, a novel compound useful as a reagent which has an excellent solubility and enables effective and accurate determination of NAGase activity and also a novel method for determining NAGase activity using the compound.

BRIEF DESCRIPTION OF THE DRAWING

FIG. 1 is a graph showing relationship between NAGase activity and change in absorbance of the formed dye at a wavelength of 490 nm per one minute in Example 3. The straight line in the Figure indicates a calibration curve.

SUMMARY OF THE INVENTION

The present inventors have made extensive study to achieve the above-mentioned object and, as a result, have found that specific, novel N-acetyl-β-D-glucosamine derivatives are extremely useful as reagents for determining NAGase activity and the above-mentioned object can be achieved by determining NAGase activity by using the derivatives. The present invention has been accomplished on the basis of above finding.

Thus, according to the present invention, there are provided an N-acetyl-β-D-glucosamine derivative [hereinafter referred to a compound (I)]represented by the formula

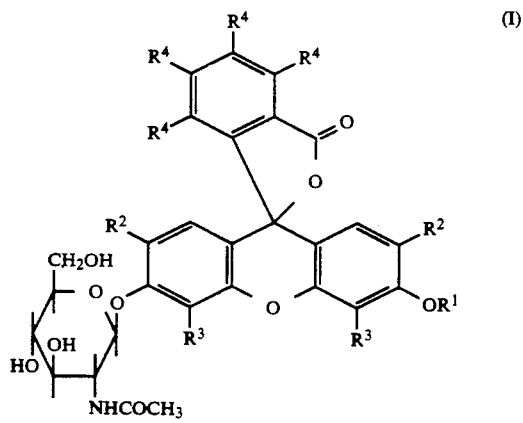

wherein $R^1$ denotes a substituted alkyl group of 1 to 4 carbon atoms having a hydroxyl group, carboxyl group, sulfonic acid group or phosphoric acid group, or an alkali metal salt thereof, or a substituted phenyl group having a hydroxyl group, carboxyl group, sulfonic acid group, phosphoric acid group or said substituted alkyl group, or an alkali metal salt thereof; and $R^2$, $R^3$ and $R^4$ each independently denote a hydrogen atom, halogen atom or nitro group, a process for producing the same, a reagent for determining NAGase activity containing the compound (I) as an effective ingredient and a method for determining NAGase activity which comprises adding the compound (I) to a sample containing NAGase and quantitatively determining aglycone (fluorescein monoethers) formed by enzyme reaction.

DETAILED DESCRIPTION OF THE INVENTION

The present invention will be described in detail below.

In the compound (I), the substituted alkyl group of 1 to 4 carbon atoms having a hydroxyl group, carboxyl group, sulfonic acid group or phosphoric acid group, or an alkali metal salt thereof, of $R^1$, may be, for example, such groups as hydroxymethyl, sulfomethyl, carboxymethyl, phosphoxymethyl, hydroxyethyl, sulfoethyl, carboxyethyl, phosphoxyethyl, hydroxypropyl, sulfopropyl, hydroxybutyl, sulfobutyl, carboxybutyl, dihydroxymethyl, phosphoxypropyl, disulfomethyl, dicarboxymethyl, dihydroxyethyl, disulfoethyl, and dicarboxyethyl, and further the sodium salts, potassium salts and like salts of these groups. As examples of the substituted phenyl group having a hydroxyl group, carboxyl group, sulfonic acid group, phosphoric acid group or said substituted alkyl group, or an alkali metal salt thereof, of $R^1$, mention may be made of such groups as hydroxyphenyl, sulfophenyl, carboxyphenyl, dihydroxyphenyl, dicarboxyphenyl, disulfophenyl, hydroxycarboxyphenyl, hydroxysulfophenyl, trihydroxyphenyl, hydroxymethylphenyl, sulfomethylphenyl, carboxymethylphenyl, phosphoxymethylphenyl, hydroxyethylphenyl, sulfoethylphenyl, carboxyethylphenyl and phosphoxyethylphenyl, and further the sodium salts, potassium salts and like salts of these groups.

The presence of the substituent $R^1$ in the compound (I) improves its solubility in water.

From the viewpoint of the solubility in water, the substituent $R^1$ is preferably a substituted alkyl group of 1 to 4 carbon atoms having a hydroxyl group, carboxyl group, sulfonic acid group or phosphoric acid group, or an alkali metal salt thereof, particularly preferably a substituted alkyl group of 1 to 4 carbon atoms having a carboxyl group, or an alkali metal salt thereof.

$R^2$, $R^3$ and $R^4$ are each independently a hydrogen atom, halogen atom (chlorine, iodine, fluorine or bromine atom) or nitro group.

From the viewpoint of the color developing property of aglycone (fluorescein monoethers) formed by the enzyme reaction of the compound (I) with NAGase, it is more preferable that at least one of the substituents $R^2$ and $R^3$ is a halogen atom and $R^4$ is a hydrogen atom.

In the compound (I), two kinds of stereoisomers at the 1-position ("spiro") carbon of the fluorescein moiety exist. Either of them, or also both of them, can be effectively used as a substrate for determining NAGase activity.

Examples of the compound (I) include 6'-O-carboxymethyl-2',7'-dichlorofluoresceinyl-N-acetyl-β-D-glucosaminide, 6'-O-carboxymethyl-4',5'-diiodofluoresceinyl-N-acetyl-β-D-glucosaminide, 6'-O-(2-hydroxyethyl)-4',5'-dibromo-2',7'-dinitrofluoresceinyl-N-acetyl-β-D-glucosaminide, 6'-O-(3-phosphoxypropyl)-fluoresceinyl-N-acetyl-β-D-glucosaminide, 6'-O-(4-sulfobutyl)-2',4',5',7'-tetraiodofluoresceinyl-N-acetyl-β-D-glucosaminide, 6'-O-(4-hydroxyphenyl)-2',4',5',7'-tetrabromofluoresceinyl-N-acetyl-β-D-glucosaminide, 6'-O-(3-sulfophenyl)-2',4',5',7'-tetraiodo-4,5,6,7-tetrachlorofluoresceinyl-N-acetyl-β-D-glucosaminide, 6'-O-(2-hydroxy-4-carboxyphenyl)-2',7'-difluorofluoresceinyl-N-acetyl-β-D-glucosaminide, 6'-O-(3-phosphoxymethylphenyl)-4',5'-dibromofluoresceinyl-N-acetyl-β-D-glucosaminide, 6'-O-(4-carboxyethylphenyl)-4,5,6,7-tetrachlorofluoresceinyl-N-acetyl-β-D-glucosaminide and the like, and further the sodium salts, potassium salts and like salts thereof.

The above-mentioned compound (I) can be prepared by reacting a halogeno-N-acetyl-D-glucosamine derivative [hereinafter referred to as compound (II)] represented by the formula

wherein X denotes an acyl group and Y denotes a halogen atom, with a fluorescein monoether [hereinafter referred to as compound (III)] represented by the formula

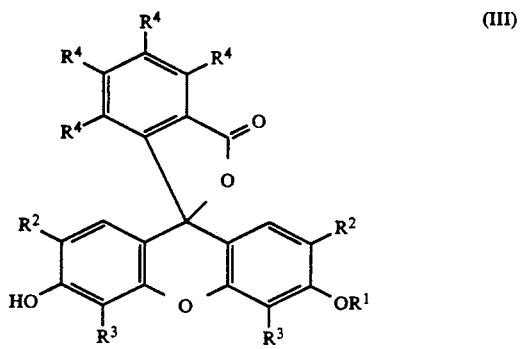

wherein $R_1$ denotes a substituted alkyl group of 1 to 4 carbon atoms having a hydroxyl group, carboxyl group, sulfonic acid group or phosphoric acid group, or an alkali metal salt thereof, or a substituted phenyl group having a hydroxyl group, carboxyl group, sulfonic acid group, phosphoric acid group or said substituted alkyl group, or an alkali metal salt thereof; and $R^2$, $R^3$ and $R^4$ each independently denote a hydrogen atom, halogen atom or nitro group, followed by de-O-acylation (as to the method of synthesis, refer, for example, to Japanese Patent Application Kokai (Laid-open) No. 1-211595).

In the compound (II), the acyl group of X is preferably that which has 2 to 5 carbon atoms, particularly preferably the acetyl group. The halogen atom of Y is preferably a chlorine atom or bromine atom.

The compound (II) can be prepared, for example, by reacting commercially available N-acetyl-D-glucosamine with an acyl halide such as acetyl chloride or acetyl bromide [J. Org. Chem., 27, 1794 (1962)]. Examples of the compound (II) include 1-chloro-1-deoxy-2,3,4,6-tetraacetyl-α-D-glucosamine, 1-bromo-1-deoxy-2,3,4,6-tetraacetyl-α-D-glucosamine and the like.

The compound (III) can be synthesized in a suitable manner by using commercially available fluoresceins, e.g., fluorescein, 2',7'-dichlorofluorescein, 4',5'-dibromofluorescein, 4',5'-diiodofluorescein, 4,5,6,7-tetrachlorofluorescein, 2',4',5',7'-tetraiodofluorescein, 4',5'-dibromo-2',7'-dinitrofluorescein, 2',4',5',7'-tetrabromo-4,5,6,7-tetrachlorofluorescein, etc. and the sodium salts, potassium salts and like salts thereof (cf., for example, J. Am. Chem. Soc., 59, 112 (1937)].

Examples of the compound (III) include 2',7'-dichlorofluorescein carboxymethyl ether, 4',5'-diiodofluorescein (dicarboxy)methyl ether, 4',5'-dibromo-2',7'-dinitrofluorescein 2-hydroxyethyl ether, fluorescein 3-phosphoxypropyl ether, 2',4',5',7'-tetraiodofluorescein 4-sulfobutyl ether, 2',4',5',7'-tetrabromofluorescein 4-hydroxyphenyl ether, 2',4',5',7'-tetraiodo-4,5,6,7-tetrachlorofluorescein 3-sulfophenyl ether, 2',7'-difluorofluorescein 2-hydroxy-4-carboxyphenyl ether, 4',5'-dibromofluorescein 3-phosphoxymethylphenyl ether, 4,5,6,7-tetrachlorofluorescein 4-(carboxyethyl)-phenyl ether, etc. and the sodium salts, potassium salts and like salts thereof.

The method of synthesis of the compound (I), for example, will be described below.

First, the compound (II) is reacted with the compound (III) in the presence of a solvent and a catalyst. The amount of the compound (II) used relative to the compound (III) is usually 1 to 50 molar equivalents, preferably 5 to 20 molar equivalents, per mole of the compound (III).

As the solvent, there may be used, for example, ketones such as acetone, methyl ethyl ketone, etc., nitriles such as acetonitrile, etc., halogenated hydrocarbons such as dichloromethane, chloroform, dichloroethane, etc., dimethylformamide (DMF), dimethylacetamide (DMA), dimethyl sulfoxide (DMSO), hexamethylphosphoramide (HMPA) and the like, or the combinations thereof. Acetonitrile is particularly preferable. The solvent is generally used in an amount of 5 to 1,000 times, preferably 50 to 500 times, the weight of the compound (III).

Examples of the catalyst which may be used include silver salts, e.g., $Ag_2O$, $AgClO_4$, $AgNO_3$, $Ag_2CO_3$, etc., mercury salts, e.g., HgO, $Hg(CN)_2$, etc., cadmium salts, e.g., $CdCO_3$, tertiary amines, e.g., triethylamine, tributylamine, etc., and the combinations of these. $Ag_2O$ is preferred. The catalyst is used generally in an amount of 1 to 10 molar equivalents, preferably 1 to 3 molar equivalents, per mole of the compound (II).

The reaction temperature and reaction time may vary depending on the kind of the compound (II), compound (III), solvent and catalyst, but the reaction is usually performed at 20° to 60° C. continuously for 1 to 60 hours.

The product thus obtained is reacted with a base to eliminate the O-acyl group, whereby the compound (I) is obtained. Examples of the base include alkali metal salts such as KOH, $K_2CO_3$, NaOH, $Na_2CO_3$, etc., alkali metal alcoholates such as sodium methylate, sodium phenolate, etc., ammonia, and the like. Particularly preferred among them is sodium methylate.

The reaction product is then purified by conventional methods to obtain the intended compound (I). As the method of purification, there may be mentioned, for example, precipitation using appropriate organic solvents and column chromatography using silica gel, ODS (octadecylsilyl silica gel), etc. The two kinds of stereoisomers of the compound (I) can be separated, if necessary and desired, by conventional means, e.g., high performance liquid chromatography.

The compound (I) thus obtained is extremely useful for determining NAGase activity. The use of the compound (I) makes it possible to determine NAGase activity with high sensitivity and high accuracy by the rate-assay method.

A system which is advantageous for determining NAGase activity is, for example, one (pH 4.0 to 6.0) which contains 1 to 20 mM of the compound (I) and 2 to 200 mM of a buffer. Examples of the buffer which may be used in the system are phosphates, acetates, citrates, succinates, phthalates, and the like. If necessary and desired, there may be added to the system as dissolution aids or stabilizers, for example, glycerol, surfactants such as Triton X-100, crown ethers, cyclodextrins or glycols.

The reagent of the present invention may be used as a dried product or in a dissolved form; it may also be used after impregnated into a thin layer carrier, for example, a sheet, impregnable paper, etc. By the use of such reagents of the present invention, the activity of NAGase contained in various samples can be determined accurately in a simple manner with high sensitivity.

Next, the method for determination of NAGase activity according to the present invention is described below by way of a preferred example.

First, 1 to 20 mM, preferably 1 to 5 mM, of the compound (I) is added to a sample containing NAGase, and a buffer is further added thereto. The resulting mixture is subjected to enzyme reaction at 30° to 60° C. for at least 1 minute, preferably at 35° to 50° C for 3 to 30 minutes at pH of 4.0 to 6.0, preferably 4.5 to 5.5. The absorbance values of aglycone (fluorescein monoethers) formed are measured directly with a spectrophotometer, from which change in absorbance per unit time is obtained. By comparing with the change in absorbance of standard NAGase previously determined in the same manner, NAGase activity in the sample can be calculated.

The NAGase-containing sample used in the present invention is not particularly limited so long as it contains NAGase. Specific examples include culture fluids of microorganisms, plant extracts, body fluids, urine and tissues of animals and extracts thereof. Examples of the buffer are phosphates, acetates, citrates, succinates, phthalates, etc. If necessary, pretreatment may be performed or an oxidizing agent is added to minimize the effect of reducible substances.

The compound (I) of the present invention is a novel compound and is extremely useful as a reagent for determining NAGase activity. By the use of the compound, NAGase activity can be determined accurately in a simple manner by means of automated analysis, manual analysis etc. without being affected by glucose, billirubin, hemoglobin and the like contained in the sample.

The present invention is further described in detail below with reference to Examples.

EXAMPLE 1

Preparation of sodio-6'-O-carboxymethyl-2',7'-dichlorofluoresceinyl-N-acetyl-β-D-glucosaminide ($R^1=CH_2CO_2Na$, $R^2=Cl$, $R^3=R^4=H$)

2',7'-Dichlorofluorescein (10.0 g, 25 mmols) was dissolved in 250 ml of methanol and 9.75 ml (50 mmols) of 28% sodium methylate-methanol solution was added to the solution. The mixture was allowed to react at room temperature for 30 minutes with stirring, and methanol was distilled off under reduced pressure to obtain dichlorofluorescein disodium salt. The product was dissolved in 750 ml of N,N-dimethylformamide, 5.6 ml (50 mmols) of ethyl bromoacetate was added to the solution, the resulting mixture was allowed to react with stirring at 80° C. for 2 hours, and then N,N-dimethylformamide was distilled off under reduced pressure. To the resulting residue was added 500 ml of water and the precipitate was collected by filtration to obtain 12.7 g of dichlorofluorescein ethoxycarbomethyl ester ethoxycarbomethyl ether. The product was suspended in ethanol (800 ml)-water (200 ml) mixture, then 40 ml of 2N-sodium hydroxide solution was added, and the mixture was allowed to react with stirring at room temperature for 2 hours. Then, ethanol was distilled off under reduced pressure, 500 ml of water was added to the residue and further 40 ml of 2N-hydrochloric acid was added. The crystals precipitated were collected by filtration and dried to give 8.55 g (yield: 74.5%) of 2',7'-dichlorofluorescein carboxymethyl ether.

Then, 40 g (109 mmols) of 1-chloro-1-deoxy-2,3,4,6-tetraacetyl-α-D-glucosamine was dissolved in 2.5 $\iota$ of acetonitrile, and 5.0 g (10.9 mmols) of 2',7'-dichlorofluorescein carboxymethyl ether and 25.3 g (109 mmols) of silver oxide ($Ag_2O$) were added to the solution. The mixture was allowed to react with stirring at 50° C. for 20 hours. Then unreacted $Ag_2O$ was filtered off. After acetonitrile in the filtrate was distilled off, the residue was purified by silica gel chromatography. The fraction eluted with a chloroform-methanol mixture (volume ratio, 4:1) was recrystallized from a chloroform-diethyl ether mixture to give 3.93 g (4.99 mmols, yield: 45.8%) of 6'-O-carboxymethyl-2',7'-dichlorofluoresceinyl-2,3,4,6-tetraacetyl-β-D-glucosaminide.

Melting point: 208° C. (decomposition)
UV and visible absorption spectra (MeOH):
Maximum absorption wavelength $[\lambda_{max}]$ = 282($\epsilon$=9300), 228($\epsilon$=55100) nm.
IR absorption spectra (KBr):
3400, 1750, 1660, 1625, 1605, 1565 $cm^{-1}$.
Nuclear magnetic resonance spectra (200 MHz) ($CDCl_3$):δ(ppm)
8.00–8.05(2H,m), 7.70–7.85(2H,m), 7.30–7.40(2H,m), 6.83(1H,s), 6.80 and 6.81(1H, each s),6.73 and 6.74(1H, each s), 5.46(1H, d, J=8.5Hz), 5.22(1H,br t, J=9.8Hz), 4.97(1H, br t,J=9.5Hz), 4.47(2H, br s), 4.10–4.30(4H, m), 2.08(3H, s), 2.01(3H, s), 1.95(3H, s), 1.74 and 1.76(3H, each s).

The 6'-O-carboxymethyl-2',7'-dichlorofluoresceinyl-2,3,4,6-tetraacetyl-β-D-glucosaminide obtained above is a mixture of two stereoisomers at the 1-position (spiro) carbon of fluorescein moiety, the abundance ratio being about 1:1 as determined from nuclear magnetic resonance spectra.

Then, 2.4 g (3.05 mmole) of 6'-O-carboxymethyl-2',7'-dichlorofluoresceinyl-2,3,4,6-tetraacetyl-β-D-glucosaminide thus obtained was dissolved in a mixture of methanol (96 ml)-chloroform (48 ml), 1.2 ml (6.2 mmols) of 28% sodium methylate-methanol solution was added thereto, and the mixture was allowed to react with stirring at room temperature for 30 minutes. Consequently, methanol and chloroform were distilled off under reduced pressure and the residue was purified by ODS (YMC●GEL ODS-AQ 120-S50, Yamamura Chemical Laboratories Co., Ltd., trademark) column chromatography. The fraction eluted with an ethanol-water mixture (volume ratio, 1:4) was lyophilized to give 1.4 g (2.05 mmols, yield: 67.2%) of sodio-6'-O-carboxymethyl-2'-7'-dichlorofluoresceinyl-N-acetyl-β-D-glucosaminide.

Melting point: 206° C. (decomposition).
UV and visible absorption spectra ($H_2O$):
Maximum absorption wavelength $[\lambda_{max}]$ = 281($\epsilon$=9000), 229($\epsilon$=55700) nm.

IR absorption spectra (KBr):
3400, 1755, 1660(sh), 1625, 1605, 1565 $cm^{-1}$.
Nuclear magnetic resonance spectra (200 MHz) (DMSO-$d_6$):δ(ppm) 8.00–8.05(1H, m), 7.70–7.85(3H,m), 7.35–7.40(1H, m), 7.31(1H, s), 6.82(1H, s), 6.74 and 6.75(1H, each s), 6.69 and 6.70(1H, each s), 5.45(2H, br s), 5.10 and 5.12(1H, each d, J=8.6Hz), 4.74(1H, br s), 4.37(2H, s), 3.75–3.90(2H, m), 3.20–3.60(4H, m), 1.77 and 1.79(3H, each s).

EXAMPLE 2

Reagent for Determining NAGase Activity (1) Composition of reagent

|  | Component | Concentration |
| --- | --- | --- |
| Substrate reagent: | Sodio-6'-O-carboxymethyl-2',7'-dichlorofluoresceinyl-N-acetyl-β-D-glucosaminide | 2.0 mM |
|  | Citrate buffer (pH = 5.0) | 50.0 mM |
|  | Purified water |  |

(2) Method of determination

After 1 ml of the substrate reagent has been heated at 37° C. for 5 minutes, 25 μl of a sample solution is added thereto. The mixture is heated at 37° C. for 5 minutes, and changes in absorbance at 490 nm during 5 minutes following said 5 minutes of heating are measured. By comparing the change in absorbance with the calibration curve previously prepared, the activity of NAGase in the sample solution can be determined.

In the case where the enzyme activity value in the sample solution exceeds the measurement limit of the calibration curve, the sample solution is diluted by a corresponding factor using 50 mM citrate buffer (pH=5.0) and the activity is measured again.

EXAMPLE 3

Method for Determining NAGase Activity (1) Preparation of substrate solution

A 1369 mg (2.0 mmols) portion of sodio-6'-O-carboxymethyl-2',7'-dichlorofluoresceinyl-N-acetyl-β-D-glucosaminide obtained in Example 1 is weighed out and 50 mM citrate buffer (pH=5.0) is added to make the whole volume 1 liter, which is used as the substrate solution.

(2) Preparation of standard NAGase solution

Commercially available NAGase solution of a known enzyme activity is diluted with 50 mM citrate buffer (pH=5.0) to several concentrations to be used as standard NAGase solution.

(3) Preparation of calibration curve

To 1 ml of the substrate solution is added 25 βl each of the standard NAGase solutions of various concentrations, and the mixture is heated at 37° C. for 5 minutes. The calibration curve is prepared based on changes in absorbance at 490 nm in 5 minutes following said heating.

When NAGase (25 u/0.5 ml) made by Sigma Co. is used, the calibration curve is expressed by the equation:

$$U = 3.55 \times (\Delta A) \times 10^3$$

wherein U represents enzyme activity and ΔA represents change in absorbance/minute. The curve is shown in the graph of FIG. 1.

(4) Determination of NAGase activity in sample solution

To 1 ml of the substrate solution is added 25 μl of a sample solution, the mixture is heated at 37° C. for 5 minutes, and change in absorbance at 490 nm during 5 minutes following said heating is measured. NAGase activity in the sample solution can be determined by comparing the change in absorbance with the calibration curve prepared in (3) above.

In the case where the enzyme activity in the sample solution is greater than the measurement limit of the calibration curve (0–500 u/ι), the sample solution is diluted by a corresponding factor using 50 mM citrate buffer (pH 5.0) and the activity is measured again.

What is claimed is:

1. An N-Acetyl-β-D-glucosamine derivative represented by the formula

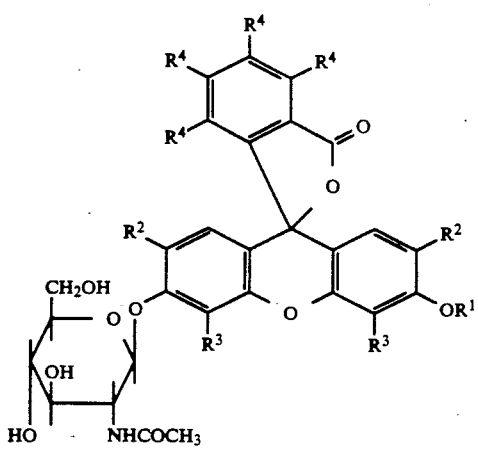

wherein $R^1$ denotes a substituted alkyl group of 1 to 4 carbon atoms having a hydroxyl group, carboxyl group, sulfonic acid group or phosphoric acid group or an alkali metal salt thereof, and $R^2$, $R^3$ and $R^4$ each independently denote a hydrogen atom, halogen atom or nitro group, and at least one of $R^2$ and $R^3$ is a halogen atom.

2. An N-Acetyl-β-D-glucosamine derivative according to claim 1, wherein $R^4$ is a hydrogen atom.

3. An N-acetyl-β-D-glucosamine derivative according to claim 2 wherein $R^1$ is a substituted alkyl group of 1 to 4 carbon atoms having a carboxyl group, or an alkali metal salt thereof.

4. An N-acetyl-β-D-glucosamine derivative according to claim 3 wherein $R^1$ is $CH_2CO_2H$ or an alkali metal salt thereof; $R^2$ is Cl; and $R^3$ and $R^4$ are each H.

5. A reagent for determination of N-Acetyl-β-D-glucosaminidase activity having pH of 4.0–6.0, containing 1–20 mM of the derivative of claim 1 and 2–200 mM of a buffer.

6. A reagent for determination of N-Acetyl-β-D-glucosaminidase activity having pH of 4.0–6.0, containing 1–20 mM of the derivative of claim 4 and 2–200 mM of a buffer.

* * * * *